(12) United States Patent
Xu et al.

(10) Patent No.: US 10,287,249 B2
(45) Date of Patent: May 14, 2019

(54) METHODS OF RESOLVING RACEMIC MIXTURE TO OBTAIN (−)-HUPERZINE A

(71) Applicant: AMPHASTAR PHARMACEUTICALS INC., Rancho Cucamonga, CA (US)

(72) Inventors: Yonggang Xu, Nanjing (CN); Hao Wei, Nanjing (CN); Song Chen, Nanjing (CN); Haoning Zhang, Nanjing (CN)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 0 days.

(21) Appl. No.: 14/752,664

(22) Filed: Jun. 26, 2015

(65) Prior Publication Data

US 2016/0096808 A1  Apr. 7, 2016

Related U.S. Application Data

(60) Provisional application No. 62/059,829, filed on Oct. 3, 2014.

(51) Int. Cl.
*C07D 221/22* (2006.01)
*C07D 471/12* (2006.01)

(52) U.S. Cl.
CPC ......... *C07D 221/22* (2013.01); *C07D 471/12* (2013.01)

(58) Field of Classification Search
CPC .......................... C07D 471/12; C07D 221/22
USPC ........................................................ 546/97
See application file for complete search history.

(56) References Cited

U.S. PATENT DOCUMENTS

2009/0247754 A1   10/2009   Underiner et al.
2015/0158817 A1   6/2015    Herzon et al.

FOREIGN PATENT DOCUMENTS

| CN | 101130520 A | 2/2008 |
| CN | 101333190 A | 12/2008 |
| CN | 102043024 A | 5/2011 |
| KR | 10-2014-0009444 A | 1/2014 |
| WO | WO 2009/120774 A1 | 10/2009 |

OTHER PUBLICATIONS

PCT/US2015/053356 International Search Report and Written Opinion dated Jan. 22, 2016, 11 pages.
Rajendran, V. et al, Synthesis, Chiral Chromatographic Separation, and Biological Activities of the Enantiomers of 10, 10-Dimethylhuperzine A, Bioorganic & Medicinal Chemistry Letters 10, 2000, pp. 2467-2469.
Tsioupi, D. et al, Chiral separation of Huperzine A using CE-Method validation and application in pharmaceutical formulations, Electrophoresis 2012, vol. 33, pp. 516-522.
Felgenhauer, N. et al, Intoxication with Huperzine A, a Potent Anticholinesterase Found in the Fir Club Moss, Journal of Toxicology: Clinical Toxicology, 2000, vol. 38, pp. 803-808.
www.alzheimersreadingroom.com/2008/07/huperzine-factsheet-alzheimers.html, Huperzine A Factsheet (Alzheimer's Disease), 8 pages.
Campiani, Giuseppe, et al., "A Palladium-Catalyzed Route to Huperzine A and Its Analogues and Their Anticholinesterase Activity," J. Org. Chem., 58, 1993, pp. 7660-7669.
Ma, Xiaoqiang, et al., "The Lycopodium alkaloids," Nat. Prod. Rep., 21, 2004, pp. 752-772.
Ma, Xiaoqiang, et al., "Is There a Better Source of Huperzine A than *Huperzia serrata*? Huperzine A Content of Huperziaceae Species in China," J. Agric. Food Chem., 53, 2005, pp. 1393-1398.
Ma, Xiaoqiang, et al., "A survey of potential huperzine A natural resources in China: The Huperziaceae," Journal of Ethnopharmacology, 2006, 104, pp. 54-67.
Qian, Ligang, et al., "A Total Synthesis of (+−)-Huperzine A," Tetrahedron Letters, 30(16), 1989, pp. 2089-2090.
Yamada, Fumio, et al., "A Route to Optically Pure (−)-Huperzine A: Molecular Modeling and in Vitro Pharmacology," J. Am. Chem. Soc., 113, 1991, pp. 4695-4696.
Zangara, Andrea, "The psychopharmacology of huperzine A: an alkaloid with cognitive enhancing and neuroprotective properties of interest in the treatment of Alzheimer's disease," Pharmacology, Biochemistry and Behavior, 75, 2003, pp. 675-686.
Alain Berthod, et al., "Cyclodextrin chiral stationary phases for liquid chromatographic separations of drug stereoisomers," Journal of Pharmaceutical & Biomedical Analysis, Great Britain, 1990, vol. 8, No. 2, pp. 123-130.
Pelayo Camps, et al., "Enantioselective synthesis of tacrine-huperzine A hybrids. Preparative chiral MPLC separation of their racemic mixtures and absolute configuration assignments by X-ray diffraction analysis," Tetrahedron: Asymmetry 9, 1998, pp. 835-849.
Pelayo Camps, et al., "Synthesis, in Vitro Pharmacology, and Molecular Modeling of Very Potent Tacrine—Huperzine A Hybrids as Acetylcholinesterase Inhibitors of Potential Interest for the Treatment of Alzheimer's Disease," J. Med. Chem. 1999, vol. 42, No. 17, pp. 3227-3242.

*Primary Examiner* — Rita J Desai
(74) *Attorney, Agent, or Firm* — Lewis Roca Rothgerber Christie LLP

(57) ABSTRACT

A method of resolving a racemic mixture of (±)-Huperzine A to (−)-Huperzine A includes: separating the (−)-Huperzine A from the racemic mixture of (±)-Huperzine A by chiral high performance liquid chromatography (HPLC), the chiral HPLC being performed utilizing a mobile phase including a solution including an alcohol and one selected from dichloromethane, trichloromethane, and a mixture thereof, and the chiral HPLC being performed utilizing a chiral stationary phase including a polysaccharide derivative.

16 Claims, 3 Drawing Sheets

METHODS OF RESOLVING RACEMIC MIXTURE TO OBTAIN (−)-HUPERZINE A

CROSS-REFERENCE TO RELATED APPLICATION(S)

The present application claims priority to and the benefit of U.S. Provisional Application No. 62/059,829, filed in the United States Patent and Trademark Office on Oct. 3, 2014, the entire content of which is incorporated herein by reference.

FIELD

Embodiments of the present disclosure relate in general to a process for the resolution of Huperzine A.

BACKGROUND

Natural Huperzine A is a chiral molecule that is also referred to as L-Huperzine A or (−)-Huperzine A. Synthetic Huperzine A may be formed as a racemic mixture referred to as (±)-Huperzine A. Huperzine A derivatives are being developed for pharmaceutical applications.

Huperzine A (HupA), which may be extracted from a club moss (e.g., *Huperzia serrata*), is a sesquiterpene alkaloid and a powerful and reversible inhibitor of acetylcholinesterase (AChE). It is believed that Huperzine A has been used in China for a century or more for the treatment of swelling, fever, and blood disorders. Huperzine A has demonstrated both memory enhancement and neuroprotective effects in animal testing and human clinical trials. Recently Huperzine A has undergone double-blind, placebo-controlled clinical trials in patients with Alzheimer's disease (AD). Significant improvements have been observed in both cognitive function and the quality of life of the participants of the clinical trials. Many of the clinical trials have been conducted in China, but HupA and its derivatives are attracting considerable interest in other countries, such as those in the Western Hemisphere, where AD is a major and growing concern.

The IUPAC name of Huperzine A is (1R,9S,13E)-1-Amino-13-ethylidene-11-methyl-6-azatricyclo[7.3.1.0]trideca-2(7),3,10-trien-5-one and the chemical structure may be illustrated as follows:

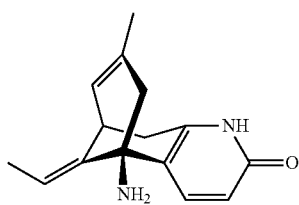

Molecular Formula of Huperzine a

Huperzine A may be isolated from many kinds of plants, such as Huperziaceae, Lycopodiaceae, and Selaginella. However, the content of Huperzine A in these plants is very low. For example, the highest content of Huperzine A among the *Huperzia* is about 0.05 wt % based on the total weight of the plant. An investigation conducted in China between 1995 and 2001 demonstrated that the content of Huperzine A in Huperziaceae varies with the harvest time and the region in which the Huperziaceae is grown. The content of Huperzine A in Huperziaceae is in a range of about 46 μg/g to about 133 μg/g. For the eleven kinds of plants that belong to Huperziaceae Phlegmariurus, which, in general, have a higher Huperzine A content than that found in other plants, the content of Huperzine A is in a range of 242 μg/g to 560 μg/g.

In addition, the growth cycle of *Huperzia serrata* is about eight to ten years. The source of natural plants including Huperzine A is limited, and the extraction rate is low. Further, cutting down trees to obtain Huperzine A will cause damage to plant cover (e.g., deforestation). With the increasing number of patients with Alzheimer's disease and the shortage of natural resources, obtaining Huperzine A from plants is no longer meeting the market demand for Huperzine A. Increasingly, synthetic Huperzine A has attracted the attention of medicinal chemists.

Synthetic Huperzine A may be obtained via many different synthetic routes. Pharmacology studies indicated that the inhibitory activity of (−)-Huperzine A, with respect to acetylcholinesterase, is more than 38-50 times that of its enantiomer (+)-Huperzine A. Hence, asymmetric synthesis and chiral resolution of (−)-Huperzine A has captured attention.

The chemical synthetic methods of obtaining Huperzine A can be divided into two main types: asymmetric synthesis and chiral resolution of racemic compounds.

The asymmetric synthesis of Huperzine A is divided into two main types: asymmetric Michael-aldol reactions and asymmetric cyclization reactions catalyzed by chiral catalysts. In an asymmetric synthesis route, chiral esters may be obtained by β-ketonic ester reacted with (−)-8-phenylmenthol via transesterification. The chiral ester may then be reacted with methacrolein-DNPH via an asymmetric Michael-aldol reaction and an aldol condensation reaction, to form an intermediate. The intermediate may be transformed to methanesulfonate, and then eliminated to a diastereoisomer which may finally be purified via chromatographic separation. The asymmetric synthesis route may be illustrated as follows:

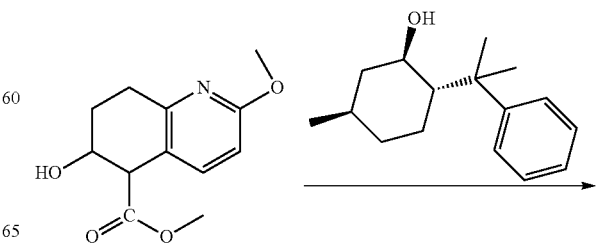

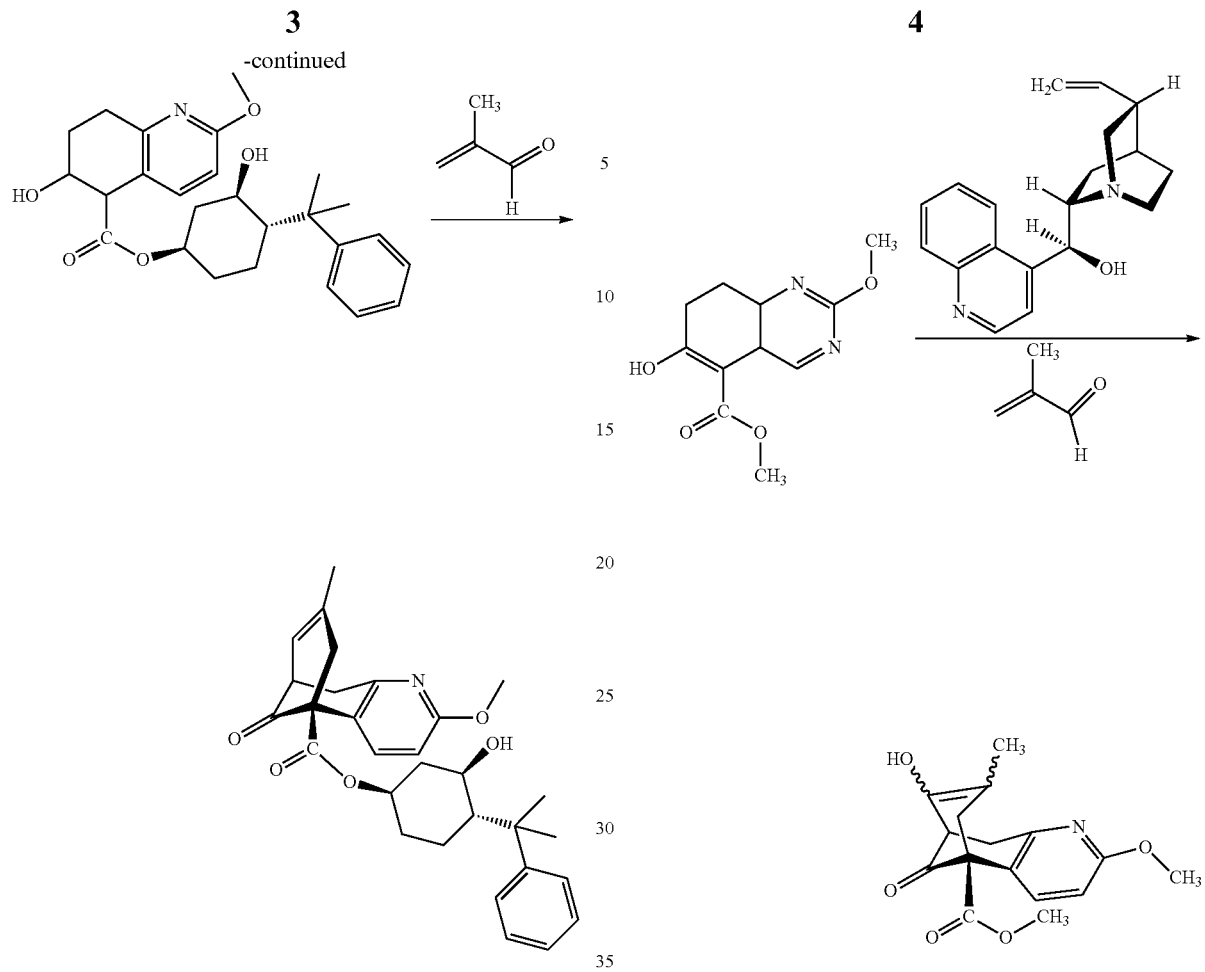

However, the above-described synthetic process is long and the yield is low. Furthermore, chromatographic separation is required and a large quantity of (−)-8-phenylmenthol is needed, and therefore, this route is not suitable for industrial production.

β-ketonic ester (β-keto ester) may also be reacted with methacrolein-DNPH via the asymmetric Michael-aldol reaction and aldol condensation reaction in the presence of a cinchona alkaloid catalyst. The reaction may be illustrated as follows:

The percent yield of the above-described reaction is only about 45% (percent yield=moles of compound 2÷moles of compound 1×100), the selectivity is low, and more than three diastereoisomers at a ratio of 10:7:1 are formed in the reaction. Therefore, dynamic axial compression chromatography is required in the post-processing.

β-ketonic ester may also react with allylpalladiumchloride dimer via an asymmetric cyclization reaction catalyzed by ferrocene. The reaction may be illustrated as follows:

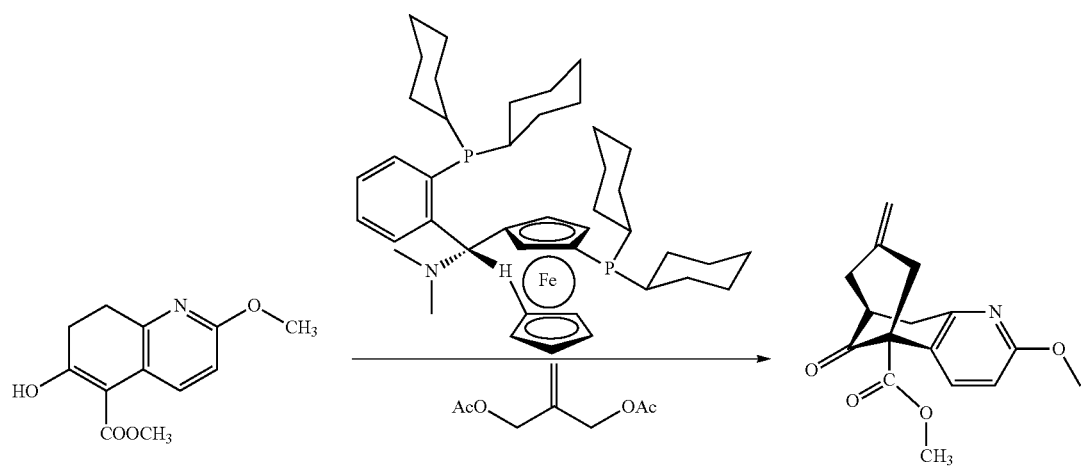

Although the selectivity of the above-described reaction is relatively higher, the ferrocene is difficult to synthesize, separate, purify and recycle. Moreover, the chiral catalyst is expensive. Accordingly, this method remains limited to laboratory applications.

The chiral resolution of Huperzine A is divided into two main types: resolution by re-crystallization and resolution by chromatography. For example, two diastereomeric salts that are generated by (−)-dibenzoyl-L-tartaric acid may be reacted with a precursor of Huperzine A. One of the two salts may be re-crystallized in an organic reagent, and Huperzine A may be obtained after dissociation. The process may be illustrated as follows:

A volume ratio of a volume of the one selected from dichloromethane, trichloromethane (chloroform), and a mixture thereof to a volume of the alcohol may be 8:1 to 1:8.

The volume ratio of the volume of the one selected from dichloromethane, trichloromethane (chloroform), and a mixture thereof to the volume of the alcohol may be 4:1 to 1:4.

The volume ratio of the volume of the one selected from dichloromethane, trichloromethane (chloroform), and a mixture thereof to the volume of the alcohol may be 2:8 to 5:8.

The mobile phase may further include an organic base at a concentration of less than 5 vol % based on the total volume of the mobile phase.

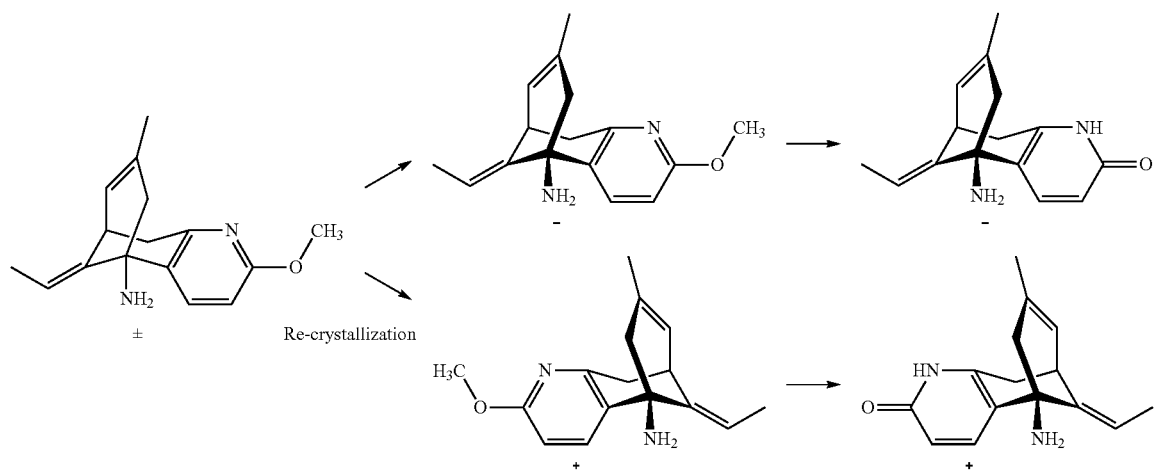

Huperzine A having high optical purity can be obtained through repeated resolutions and purification, but the process is cumbersome and the yield is very low (e.g., a percent yield of approximately 16.2%; percent yield=mass of (−)-Huperzine A in final product÷mass of (±) Huperzine A in the racemic mixture×100).

SUMMARY

Embodiments of the present disclosure are directed toward a method for preparing optically purified (−)-Huperzine A. According to embodiments of the present disclosure, Huperzine A and its enantiomer may be separated by preparative, chiral High Performance Liquid Chromatography (HPLC). Embodiments of the present disclosure relate in general to a process for the resolution of synthetic Huperzine A (e.g., a racemic mixture referred to as (±)-Huperzine A) to obtain substantially optically pure (−)-Huperzine A.

An embodiment of a method of resolving a racemic mixture of (±)-Huperzine A to (−)-Huperzine A includes: separating the (−)-Huperzine A from the racemic mixture of (±)-Huperzine A by chiral high performance liquid chromatography (HPLC), the chiral HPLC being performed utilizing a mobile phase including a solution including an alcohol and one selected from dichloromethane, trichloromethane (chloroform), and a mixture thereof, and the chiral HPLC being performed utilizing a chiral stationary phase including a polysaccharide derivative.

The alcohol may be selected from primary alcohols having 1 to 6 carbon atoms, secondary alcohols having 1 to 6 carbon atoms, and mixtures thereof.

The alcohol may include methanol, ethanol, isopropanol, or a mixture thereof.

The organic base may be included in the mobile phase at a concentration of 0.1 vol % to 5 vol % based on the total volume of the mobile phase.

The organic base may be included in the mobile phase at a concentration of 0.3 vol % to 0.5 vol % based on the total volume of the mobile phase.

The organic base may include ethanediamine, diethylamine, triethylamine, or a mixture thereof. For example, the organic base may include diethylamine.

The polysaccharide derivative of the chiral stationary phase may include amylose tris(3,5-dimethylphenyl carbamate), cellulose tris(3,5-dimethylphenyl carbamate), cellulose tris(3,5-dichloro-phenylcarbamate), or a mixture thereof. For example, the polysaccharide derivative of the chiral stationary phase may include cellulose tris(3,5-di-chloro-phenyl carbamate).

The chiral stationary phase may include particles including the polysaccharide derivative, the particles having an average particle diameter of 5 μm to 20 μm. For example, the average particle diameter of the particles may be 10 μm to 20 μm.

The method may further include: preparing two solutions by dissolving the racemic mixture including (±)-Huperzine A into the mobile phase to a concentration in a range of 0.05 g/ml to 0.3 g/ml, where a ratio of a flow rate of the chiral HPLC in ml/min to a column diameter of a chiral column of the chiral HPLC in mm is 1.2 to 3.5; injecting one of the solutions into an injection port of a chiral high performance liquid chromatograph including the chiral column, where a ratio of an injection volume of the solution in ml to the column diameter of the chiral high performance liquid chromatograph in mm is 0.02 to 0.6; and collecting the resultant (−)-Huperzine A.

The method may further include spin-drying the resultant (−)-Huperzine A.

The chiral HPLC may be performed utilizing an ultraviolet light detector.

The ultraviolet light detector may detect a wavelength of ultraviolet light of 210 to 310 nm.

A temperature of the chiral column may be 20 to 30° C.

As compared to other technologies for producing (−)-Huperzine A, embodiments of the present disclosure have the following features: the time for the separation process is relatively short; the active acts of the method are simple and the final optical purity or enantiomeric excess (ee) is high (e.g., the value of ee of (−)-Huperzine A may be about 99.0% or more, or 99.5% or more, where the value of ee is calculated by dividing the peak area (area %) of the (−)-Huperzine A the total peak area of (−)-Huperzine A and (+)-Huperzine A as measured by high performance liquid chromatography); and the yield is relatively high (e.g., a percent yield of about 48% or more, such as 48% to 50%; percent yield=mass of (−)-Huperzine A in final product divided by mass of (±)-Huperzine A in the racemic mixture× 100).

According to the resolution technology utilized in embodiments of the present disclosure, the chiral column of chiral of the high performance liquid chromatograph may be packed with a material that may be utilized 1500~2000 times, thereby reducing the cost of embodiments of the method. The cost of embodiments of the present disclosure is lower than that associated with the production of (−)-Huperzine A utilizing chiral catalysts (e.g., the cost for the material for packing the HPLC column is about 5% of the overall material costs for an example of the chiral synthesis).

BRIEF DESCRIPTION OF THE DRAWINGS

The accompanying drawings, together with the specification, illustrate embodiments of the present disclosure, and, together with the description, serve to explain the principles of the present disclosure.

DETAILED DESCRIPTION

Figure 1:
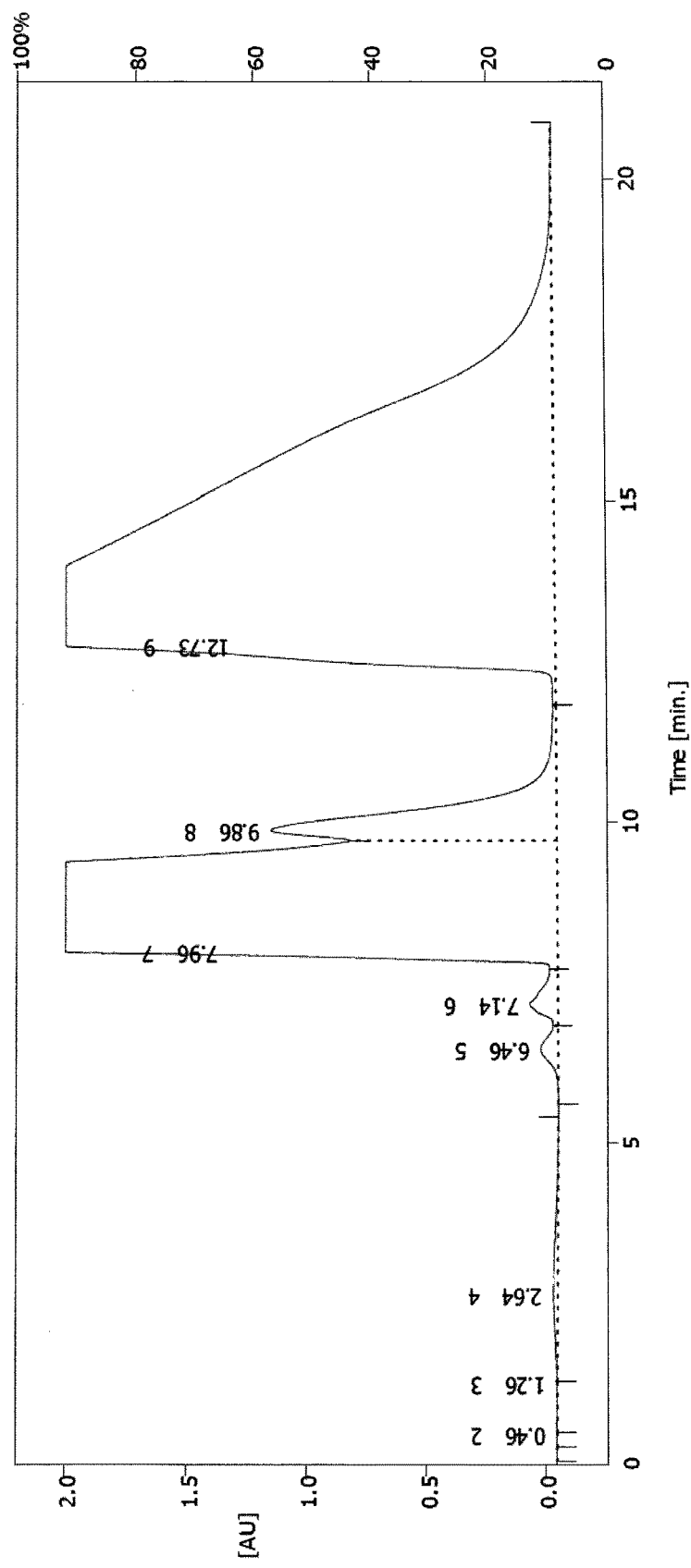
FIG. 1 is a graph showing a chiral resolution chromatogram of the racemic mixture of (±)-Huperzine A separated into (−)-Huperzine A in Example 2.

The following detailed description is provided only for purposes of illustration of certain specific embodiments of the present disclosure and not for purposes of limiting the scope of the present disclosure. Alternate embodiments will be readily apparent to those of skill in the art and are intended to be included within the scope of the present disclosure. Also, in the context of the present application, the term "Huperzine A" is used in a broad sense and encompasses any form of Huperzine A or Huperzine A analogue that can be utilized to treat a human or animal. For example, as used herein, the term "Huperzine A" encompasses natural or synthetic (−)-Huperzine A and derivatives thereof.

As used herein, the terms "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a) and 35 U.S.C. § 132(a).

Embodiments of the present disclosure are directed toward a method for resolving racemic Huperzine A by way of industrial-scale, preparative, chiral High-Performance Liquid Chromatography (HPLC). For example, embodiments of the method include separating synthetic Huperzine A by preparative, chiral HPLC. Embodiments of the method are efficient and have simple operation. Both the yield and final optical purity (−)-Huperzine A obtained by embodiments of the method are high. For example, (−)-Huperzine A obtained by embodiments of the method has a final optical purity or enantiomeric excess of 99.0% or more (e.g., the product may include up to 99.0 mol % of (−)-Huperzine A, based on the total moles of (−)-Huperzine A and (+)-Huperzine A), and the enantiomeric excess (ee) may be 99.8% or more (e.g., up to 99.8 mol % of (−)-Huperzine A, based on the total moles of (−)-Huperzine A and (+)-Huperzine A). For example, the value of ee of (−)-Huperzine A may be about 99.0% or more, or 99.5% or more, where the value of ee is calculated by dividing the peak area (area %) of the (−)-Huperzine A by the total peak area of (−)-Huperzine A and (+)-Huperzine A as measured by high performance liquid chromatography (HPLC). According to embodiments of the method, the percent yield of chiral separation step is about 48% to 50% (percent yield=mass of (−)-Huperzine A in final product divided by mass of (±)-Huperzine A in the racemic mixture×100), which is nearly identical with the theoretical yield.

According to an embodiment, a method of resolving a racemic mixture of (±)-Huperzine A to (−)-Huperzine A includes: separating the (−)-Huperzine A from the racemic mixture of (±)-Huperzine A by chiral high performance liquid chromatography (HPLC), the chiral HPLC being performed utilizing a mobile phase comprising a solution comprising an alcohol and one selected from dichloromethane, trichloromethane (chloroform), and a mixture thereof, and the chiral HPLC being performed utilizing a chiral stationary phase comprising a polysaccharide derivative.

Huperzine A and its enantiomer may be prepared according to any suitable process available in the art. For example, Huperzine A and its enantiomer may be prepared as described in Campiani G., Sun L. Q., Kozikowski A. P., "A Palladium-catalyzed route to Huperzine A and Its Analogues and Their Anticholinesterase Activity," *J. Org. Chem.*, 1993, 58, 7660, the entire content of which is incorporated by reference herein. For example, racemic Huperzine A may be prepared by utilizing β-keto ester as a raw material. The racemate may be separated by industrial-scale preparative HPLC. The synthetic route may be illustrated as follows:

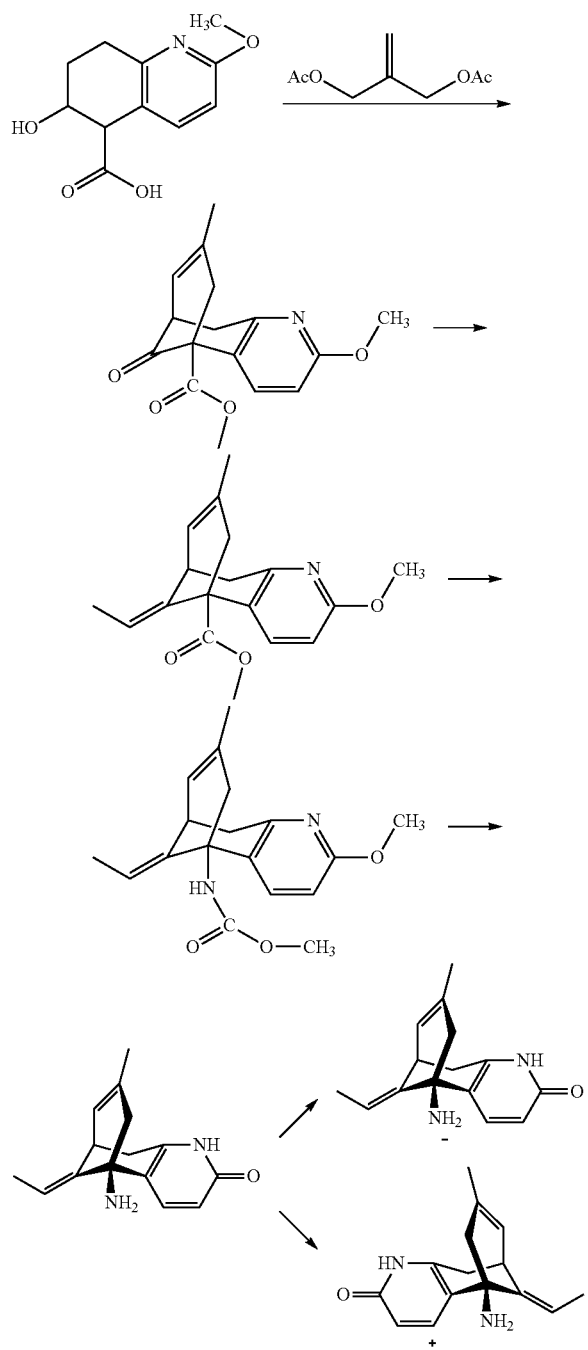

In some embodiments, a chromatographic column (a chiral column) of a chiral high performance liquid chromatograph includes a fiber and is chiral. The chiral HPLC may be performed utilizing a mobile phase including the one selected from dichloromethane, trichloromethane (chloroform), and a mixture thereof. The mobile phase may also include the alcohol (e.g., a low alcohol). For example, the mobile phase of the chiral HPLC process may include dichloromethane, trichloromethane (chloroform), and/or the alcohol (e.g., the low alcohol). The mobile phase may further include an organic base. The alcohol (e.g., the low alcohol) may include a primary alcohol having 1 to 6 carbon atoms, a secondary alcohol having 1 to 6 carbon atoms, or a mixture thereof. For example, the alcohol may include methanol, ethanol, isopropanol, or a mixture thereof. The organic base may include ethanediamine, diethylamine, triethylamine, or a mixture thereof. For example, the organic base may include diethylamine.

A volume ratio of a volume of the one selected from dichloromethane, trichloromethane (chloroform), and a mixture thereof (e.g., a volume of the dichloromethane, a volume of the trichloromethane (chloroform), and/or a volume of a mixture thereof) to a volume of the alcohol may be in a range of 8:1 to 1:8. For example, the volume ratio of the volume of the one selected from dichloromethane, trichloromethane (chloroform), and a mixture thereof (e.g., the volume of the dichloromethane, the volume of the trichloromethane (chloroform), and/or a volume of a mixture thereof) to the volume of the alcohol may be in a range of 4:1 to 1:4, or 2:8 to 5:8. The mobile phase may include the organic base at a concentration of less than 5 vol % based on the total volume of the mobile phase. The concentration (V/V) of the organic base in the mobile phase may be in a range of 0.1 vol % to 5 vol % based on the total volume of the mobile phase. For example, the concentration of the organic base in the mobile phase may be in a range of 0.1 vol % to 0.5 vol %, or 0.3 vol % to 0.5 vol %.

In certain embodiments, the polysaccharide derivative of the chiral stationary phase (e.g., the polysaccharide-base chiral stationary phases) includes a material selected from amylose tris(3,5-dimethylphenyl carbamate), cellulose tris (3,5-dimethylphenyl carbamate), and cellulose tris(3,5-dichlorophenyl carbamate), and a mixture thereof. For example, the polysaccharide derivative of the chiral stationary phase may include cellulose tris(3,5-dichlorophenyl carbamate).

The chiral column (e.g., the chiral chromatography column) may include a fiber and may be chiral. The chiral column (e.g., the chiral chromatography column) may be manually filled or may be commercially selected (e.g., may be selected from commercially available chiral columns). The average particle diameter of the packing material of the chiral column may be selected to be 5 µm to 20 µm, or 10 µm to 20 µm. The diameter of the chiral column may be selected to be 1 cm to 10 cm (e.g., 2 cm to 5 cm). For example, the diameter of the chiral column may be 5 cm.

In certain embodiments, the preparative, chiral High-Performance Liquid Chromatography (preHPLC) is industrial-scale and is suitable for industrial production of (−)-Huperzine A.

A flow rate of the mobile phase may be selected based on the dimensions of the chiral column. Any flow rate suitable for the dimensions of the chiral column may be utilized. For example, when the chiral column has dimensions of 250 mm (length)×50 mm (width or diameter), the flow rate of the mobile phase may be 60 ml/min to 120 ml/min, or 80 ml/min to 100 ml/min. Suitable flow rates for chiral columns having other dimensions may be determined from the relationship between the foregoing flow rate and chiral column dimensions. For example, the flow rate may be set according to a formula: flow rate (ml/min)÷the column diameter (mm) ratio=1.2 to 3.5. Embodiments of the chiral HPLC may utilize an ultra violet light detector (a UV-detector). The UV-detector may be utilized to identify and/or quantify the components that are separated by the chiral HPLC. For example, the UV-detector may be utilized to detect a wavelength of UV light that is reflected, transmitted, and/or absorbed by the components separated by the chiral HPLC.

The ultraviolet light detector may detect a wavelength of ultraviolet of 210 nm to 310 nm (e.g., between 210 nm and 310 nm). For example, the wavelength detected by the UV-detector may be 240 nm to 280 nm (e.g., between 240 nm and 280 nm). In some embodiments, the UV-detector detects a wavelength of UV light of 254 nm that is reflected, transmitted, and/or absorbed by the components separated by the chiral HPLC.

Embodiments of the present disclosure are characterized by the following acts:

(1) Preparing two solutions by dissolving the mixture including racemic (±)-Huperzine A into the mobile phase to a concentration in a range of 0.05 g/ml to 0.3 g/ml.

(2) The flow rate being set according to the formula: flow rate (ml/min)÷the column diameter (mm) ratio=1.2 to 3.5. The wavelength of the UV-detector may be 254 nm, and the separating may be performed at a temperature of 20 to 30° C. (e.g., the chiral column may be at a temperature in a range of 20 to 30° C., such as a temperature of 30° C.).

(3) Injecting one of the solutions prepared in (1) into an injection port of a preparative, chiral High-Performance Liquid Chromatograph. The injection volume may be calculated according to a formula: injection volume (ml)÷column diameter (mm)=0.02 to 0.6.

(4) Collecting the resultant (−)-Huperzine A. Optically pure or substantially optically pure (−)-Huperzine A may be obtained spin-drying the resultant (−)-Huperzine A.

The present disclosure is not limited to obtaining (−)-Huperzine A through the resolution of racemic (±)-Huperzine A. For example, embodiments of the present disclosure may also be utilized to analyze the optical purity of Huperzine A.

Embodiments of the method may be illustrated by the following examples, which are set forth to illustrate certain embodiments of the present disclosure and are not to be construed as limiting.

Example 1

Racemic (±)-Huperzine A was prepared as described in Campiani G., Sun L. Q., Kozikowski A. P., "A Palladium-catalyzed route to Huperzine A and Its Analogues and Their Anticholinesterase Activity," *J. Org. Chem.*, 1993, 58, 7660, by utilizing the β-ketonic ester (the β-ketonic ester) as a raw material.

Example 2

The racemate ((−)-Huperzine A) was separated from the racemic mixture of (±)-Huperzine A of Example 1 by industrial-scale, preparative, chiral HPLC. FIG. 1 is a graph showing the chiral resolution chromatogram of the racemic mixture of (±)-Huperzine A separated into (−)-Huperzine A in Example 2. The experimental conditions (e.g., instruments and conditions) were as follows:

Equipment: Industrial-scale Preparative High-Performance Liquid Chromatograph (Pilot 6000), obtained from Beijing Tong Heng Innovation Technology Co., Ltd. (Beijing, China) including a DAC 50 chiral column. The maximum flow velocity was 500 ml/min.

The chiral column: DAC50 column obtained from Interchim (Montlucon, France) having dimensions of 250 mm (length)×50 mm (diameter).

The chiral column packing material: cellulose tris(3,5-dichlorophenyl carbamate) having an average particle diameter of 10 μm.

The chiral column temperature: 30° C.

The wavelength of UV-detector: 254 nm.

The mobile phase: Solution including methanol and dichloromethane (at a volume ratio of 20/80), and including diethylamine in an amount of 0.5% (V/V based on the total volume of the mobile phase).

The flow rate: 80 ml/min.

The injection volume: 20 ml.

The cellulose tris(3,5-dichlorophenyl carbamate) was filled into the DAC50 column according to the instructions provided by Interchim. The DAC50 column is a chiral column, and was connected to the industrial-scale Preparative High-Performance Liquid Chromatograph (HPLC) obtained from Beijing Tong Heng Innovation Technology Co., Ltd. 20 g of the racemic mixture of (±)-Huperzine A of Example 1 was dissolved in the mobile phase to prepare 100 ml of a sample solution (the 20 g of the racemic mixture of (±)-Huperzine A was diluted in the mobile phase to 100 ml).

Under the above-identified conditions, the sample solution was injected into the preparative, chiral HPLC. The sample solution was separated into (−)-Huperzine A and (+)-Huperzine A and the chromatogram was recorded. The chiral resolution chromatogram of the racemic mixture of (±)-Huperzine A under the conditions of Example 2 is shown in FIG. 1.

The components corresponding to the signals in FIG. 1 appearing at 7.5 minutes to 9.8 minutes, and at 12.5 minutes to 20 minutes, respectively, were collected. The former (the component corresponding to the signal at 7.5 minutes to 9.8 minutes) included the enantiomer of Huperzine A ((+)-Huperzine A), and the latter (the component corresponding to the signal at 12.5 minutes to 20 minutes) included Huperzine A ((−)-Huperzine A). The (−)-Huperzine A was spun dry. The mass of the (−)-Huperzine A after spin drying was 1.85 g. The optical purity of the (−)-Huperzine A after spin drying was analyzed utilizing an Agilent 1260 Infinity Quaternary LC System (obtained from Agilent, Santa Clara, Calif.), which provided a test value enantiomeric excess (ee) of 99.8% (99.8 mol % of (−)-Huperzine A, based on the total moles of (−)-Huperzine A and (+)-Huperzine A), as measured by HPLC.

Example 3

Figure 2:
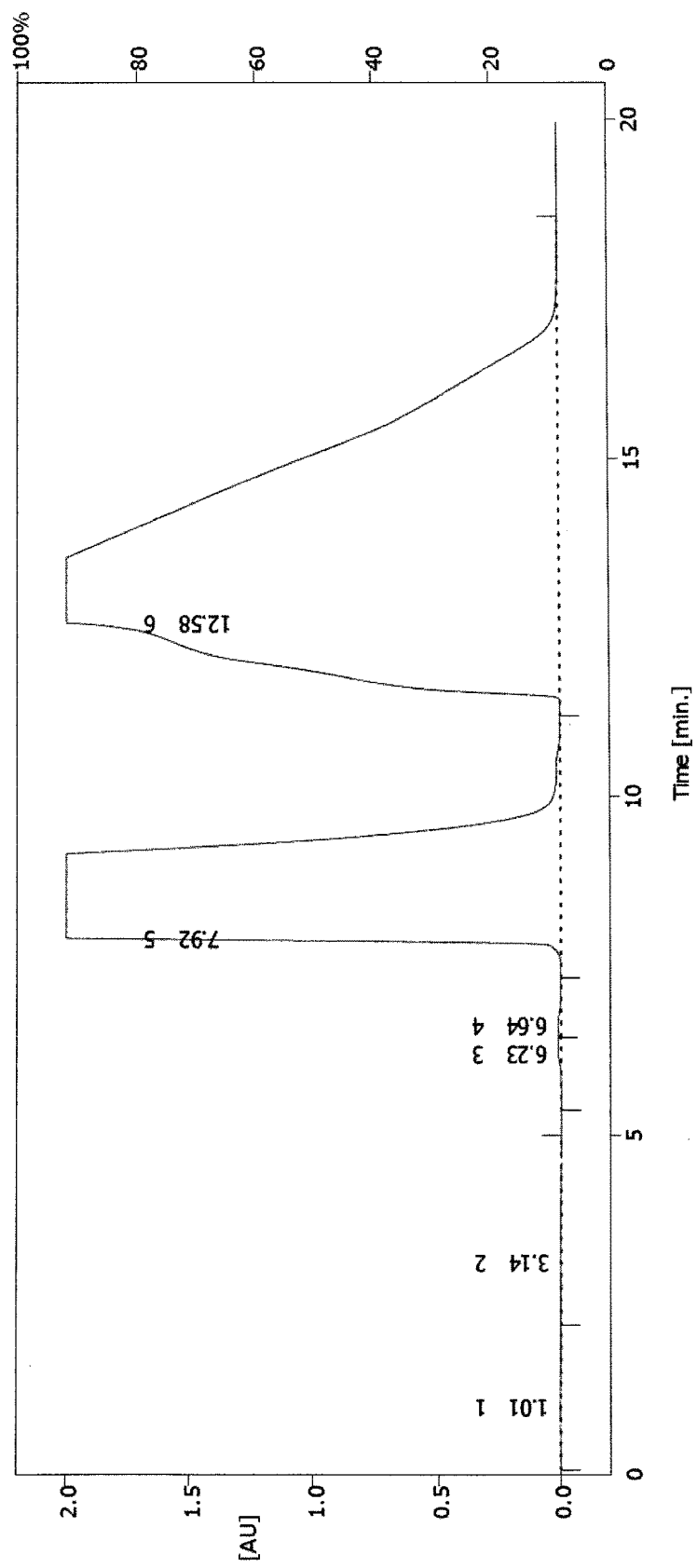
FIG. 2 is a graph showing a chiral resolution chromatogram of the racemic mixture of (±)-Huperzine A separated into (−)-Huperzine A in Example 3

The racemate (−)-Huperzine A was separated from the racemic mixture of (±)-Huperzine A of Example 1 by industrial-scale Preparative, chiral HPLC. FIG. 2 is a graph showing the chiral resolution chromatogram of the racemic mixture of (±)-Huperzine A separated into (−)-Huperzine A in Example 3. The experimental conditions (e.g., instruments and conditions) were as follows:

Equipment: Industrial-scale Preparative High-Performance Liquid Chromatograph (Pilot 6000), obtained from Beijing Tong Heng Innovation Technology Co., Ltd. (Beijing, China) including a DAC 50 chiral column. The maximum flow velocity was 500 ml/min.

The chiral column: DAC50 column obtained from Interchim (Montlucon, France) having dimensions of 250 mm (length)×50 mm (diameter).

The chiral column packing material: cellulose tris(3,5-dichlorophenyl carbamate) having an average particle diameter of 10 μm.

The chiral column temperature: 30° C.

The wavelength of UV-detector: 254 nm.

The mobile phase: Solution including methanol and dichloromethane (at a volume ratio of 40/60), and including diethylamine in an amount of 0.5% (V/V based on the total volume of the mobile phase).

The flow rate: 80 ml/min.

The injection volume: 20 ml.

The cellulose tris(3,5-dichlorophenyl carbamate) was filled into the DAC50 column according to the instructions provided by Interchim. The DAC50 is a chiral column, and was connected to the industrial-scale Preparative HPLC obtained from Beijing Tong Heng Innovation Technology Co., Ltd. 20 g of the racemic mixture of (±)-Huperzine A of Example 1 was dissolved in the mobile phase to prepare 100 ml of a sample solution (the 20 g of the racemic mixture of (±)-Huperzine A was diluted in the mobile phase to 100 ml).

Under the above-identified conditions, the sample solution was injected into the preparative, chiral HPLC. The sample solution was separated into (−)-Huperzine A and (+)-Huperzine A and the chromatogram was recorded. The chiral resolution chromatogram of the racemic mixture of (±)-Huperzine A under the conditions of Example 3 is shown in FIG. 2.

The components corresponding to the signals in FIG. 2 appearing at 7.5 minutes to 11.0 minutes, and at 11.5 minutes to 20 minutes, respectively, were collected. The former (the component corresponding to the signal at 7.5 minutes to 11.0 minutes) included the enantiomer of Huperzine A ((+)-Huperzine A), and the latter (the component corresponding to the signal at 11.5 minutes to 20 minutes) included Huperzine A ((−)-Huperzine A). The (−)-Huperzine A was spun dry. The mass of the (−)-Huperzine A after spin drying was 1.88 g. The optical purity of the (−)-Huperzine A after spin drying was analyzed utilizing an Agilent 1260 Infinity Quaternary LC System (obtained from Agilent, Santa Clara, Calif.), which provided a test value enantiomeric excess (ee) of 99.8% (99.8 mol % of (−)-Huperzine A based on the total moles of (−)-Huperzine A and (+)-Huperzine A), as measured by HPLC.

Example 4

Figure 3:
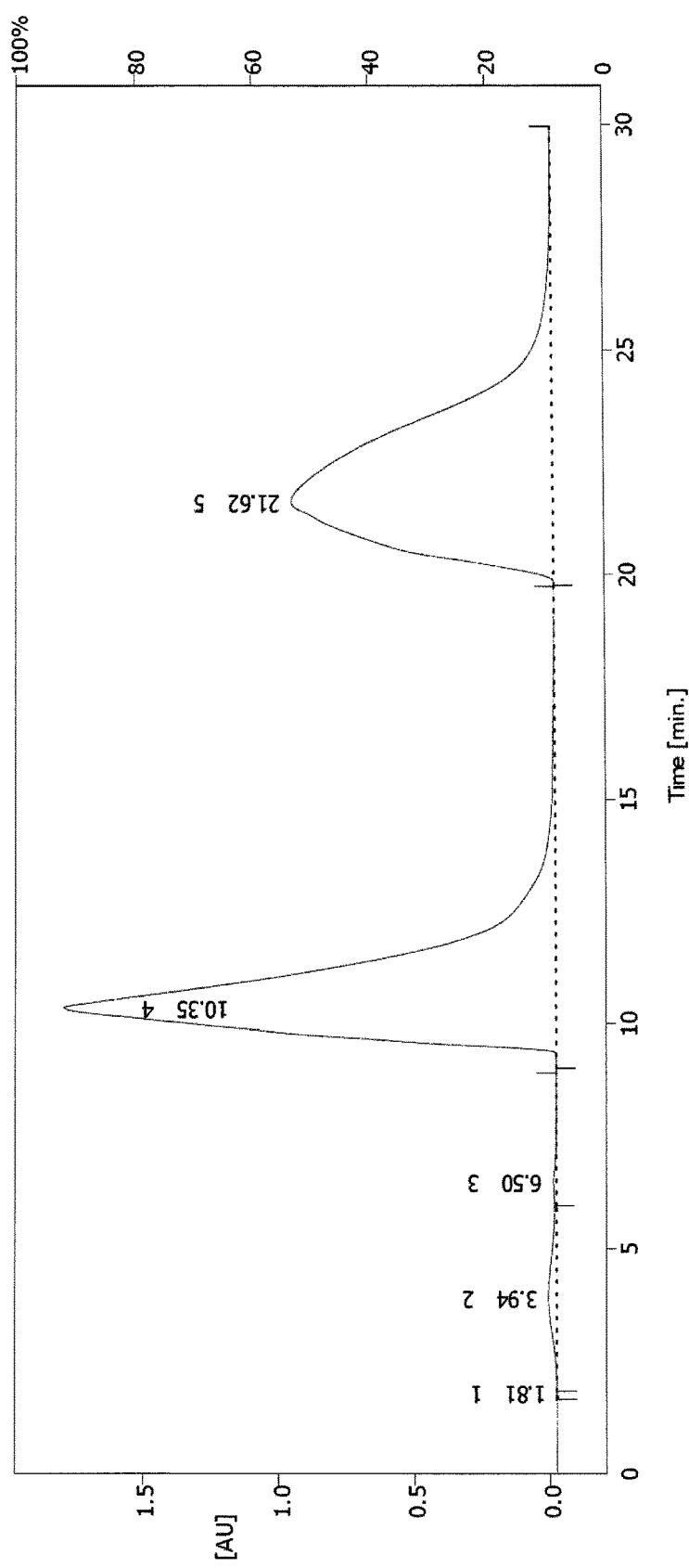
FIG. 3 is a graph showing a chiral resolution chromatogram of the racemic mixture of (±)-Huperzine A separated into (−)-Huperzine A in Example 4.

The racemate (−)-Huperzine A was separated from the racemic mixture of (±)-Huperzine A of Example 1 by industrial-scale Preparative, chiral HPLC. FIG. 3 is a graph showing the chiral resolution chromatogram of the racemic mixture of (±)-Huperzine A separated into (−)-Huperzine A in Example 4. The experimental conditions (e.g., instruments and conditions) were as follows:

Equipment: Industrial-scale Preparative High-Performance Liquid Chromatography (Pilot 6000), obtained from Beijing Tong Heng Innovation Technology Co., Ltd. (Beijing, China) including a DAC 50 chiral column. The maximum flow velocity was 500 ml/min.

The chiral column: DAC50 column obtained from Interchim (Montlucon, France) having dimensions of 250 mm (length)×50 mm (diameter).

The chiral column packing material: cellulose tris(3,5-dichlorophenyl carbamate) having an average particle diameter of 10 µm.

The chiral column temperature: 30° C.

The wavelength of UV-detector: 254 nm.

The mobile phase: Solution including methanol and dichloromethane (at a volume ratio of 80/20), and including diethylamine in an amount of 0.5% (V/V based on the total volume of the mobile phase).

The flow rate: 80 ml/min.

The injection volume: 20 ml.

The cellulose tris(3,5-dichlorophenyl carbamate) was filled into the DAC50 column according to the instructions provided by Interchim. DAC50 column is a chiral column, and was connected to the industrial-scale Preparative HPLC obtained from Beijing Tong Heng Innovation Technology Co., Ltd. 5 g of the racemic mixture of (±)-Huperzine A was diluted in the mobile phase to prepare 100 ml of a sample solution (the 5 g of the racemic mixture of (±)-Huperzine A was diluted in the mobile phase to 100 ml).

Under the above-identified conditions, the sample solution was injected into the preparative, chiral HPLC. The sample solution was separated into (−)-Huperzine A and (+)-Huperzine A and the chromatogram was recorded. The chiral resolution chromatogram of the racemic mixture of (±)-Huperzine A under the conditions of Example 4 is shown in FIG. 3.

The components corresponding to the signals in FIG. 3 appearing at 9.5 minutes to 15.5 minutes, and at 19.5 minutes to 30 minutes, respectively, were collected. The former (the component corresponding to the signal at 9.5 minutes to 15.5 minutes) included the enantiomer of Huperzine A ((+)-Huperzine A), and the latter (the component corresponding to the signal at 19.5 minutes to 30 minutes) included Huperzine A ((−)-Huperzine A). The (−)-Huperzine A was spun dry. The mass of the (−)-Huperzine A after spin drying was 0.48 g. The optical purity of the (−)-Huperzine A after spin drying was analyzed utilizing an Agilent 1260 Infinity Quaternary LC System (obtained from Agilent, Santa Clara, Calif.), which provided a test value enantiomeric excess (ee) of 99.8% (It means that the value of (−)-Huperzine A peak area minus (+)-Huperzine A peak area divide the total peak area of (−)-Huperzine A and (+)-Huperzine A is 99.8%), as measured by HPLC.

According to embodiments of the present disclosure: the time for the process of separating (−)-Huperzine A is relatively short; the active acts of the method are simple and the final optical purity or enantiomeric excess (ee) of (−)-Huperzine A is high (e.g., the value of ee of (−)-Huperzine A is about 99.0% or more, or 99.5% or more, where the value of ee is calculated by dividing the peak area (area %) of the (−)-Huperzine A by the total peak area of (−)-Huperzine A and (+)-Huperzine A as measured by high performance liquid chromatography (HPLC)); and the yield of (−)-Huperzine A is relatively high (e.g., a percent yield of (−)-Huperzine A of about 48% or more, such as 48% to 50%; percent yield=mass of (−)-Huperzine A in final product divided by mass of (±)-Huperzine A in the racemic mixture×100).

While the present disclosure has been described in connection with certain embodiments, it is to be understood that the disclosure is not limited to the disclosed embodiments, but, on the contrary, is intended to cover various modifications and equivalent arrangements included within the spirit and scope of the appended claims, and equivalents thereof. Throughout the text and claims, the terms "about" and "substantially" are used as terms of approximation, not terms of degree, and reflect the inherent variation associated with measurement, significant figures, and interchangeability, all as understood by a person having ordinary skill in the relevant art. Also, it is to be understood that throughout this disclosure and the accompanying claims, even values that are not preceded by the term "about" are also implicitly modified by that term, unless otherwise specified.

What is claimed is:

1. A method of resolving a racemic mixture of (±)-Huperzine A to (−)-Huperzine A, the method comprising:
separating the (−)-Huperzine A from the racemic mixture of (±)-Huperzine A by chiral high performance liquid chromatography (HPLC), the chiral HPLC being performed utilizing a mobile phase consisting of methanol, dichloromethane, and diethylamine, and the chiral HPLC being performed utilizing a chiral stationary phase comprising a polysaccharide derivative, wherein the enantiomeric excess of the resultant (−)-Huperzine A is 99.0% or more, the enantiomeric excess being calculated by dividing the peak area of the (−)-Huperzine A by the total peak area of the (−)-Huperzine A and the (+)-Huperzine A.

2. The method of claim 1, wherein a volume ratio of a volume of the dichloromethane to a volume of the methanol is 8:1 to 1:8.

3. The method of claim 2, wherein the volume ratio of the volume of the dichloromethane to the volume of the methanol is 4:1 to 1:4.

4. The method of claim 3, wherein the volume ratio of the volume of the dichloromethane to the volume of the methanol is 2:8 to 5:8.

5. The method of claim 1, wherein the mobile phase comprises the diethylamine at a concentration of less than 5 vol % based on the total volume of the mobile phase.

6. The method of claim 5, wherein the diethylamine is included in the mobile phase at a concentration of 0.1 vol % to 5 vol % based on the total volume of the mobile phase.

7. The method of claim 5, wherein the diethylamine is included in the mobile phase at a concentration of 0.3 vol % to 0.5 vol % based on the total volume of the mobile phase.

8. The method of claim 1, wherein the polysaccharide derivative of the chiral stationary phase comprises amylose tris(3,5-dimethylphenyl carbamate), cellulose tris(3,5-dimethylphenyl carbamate), cellulose tris(3,5-dichloro-phenyl carbamate), or a mixture thereof.

9. The method of claim 8, wherein the polysaccharide derivative of the chiral stationary phase comprises cellulose tris(3,5-dichloro-phenyl carbamate).

10. The method of claim 8, wherein the chiral stationary phase comprises particles comprising the polysaccharide derivative, the particles having an average particle diameter of 5 μm to 20 μm.

11. The method of claim 10, wherein the average particle diameter of the particles is 10 μm to 20 μm.

12. The method of claim 1, further comprising:
preparing two solutions by dissolving the racemic mixture comprising (±)-Huperzine A into the mobile phase to a concentration in a range of 0.05 g/ml to 0.3 g/ml, wherein a ratio of a flow rate of the chiral HPLC in ml/min to a column diameter of a chiral column of the chiral HPLC in mm is 1.2 to 3.5;

injecting one of the solutions into an injection port of a high performance liquid chromatograph including the chiral column, wherein a ratio of an injection volume of the solution in ml to the column diameter of the chiral high performance liquid chromatograph in mm is 0.02 to 0.6; and collecting the resultant (−)-Huperzine A.

13. The method of claim 12, further comprising spin-drying the resultant (−)-Huperzine A.

14. The method of claim 12, wherein the chiral HPLC is performed utilizing an ultraviolet light detector.

15. The method of claim 14, wherein the ultraviolet light detector detects a wavelength of ultraviolet light of 210 to 310 nm.

16. The method of claim 12, wherein a temperature of the chiral column is 20 to 30° C.

* * * * *